United States Patent [19]
Boss et al.

[11] Patent Number: 5,741,635
[45] Date of Patent: Apr. 21, 1998

[54] METHOD OF QUANTITATING GTP AND GDP BOUND TO A G PROTEIN AND USES THEREOF

[75] Inventors: Gerry R. Boss, La Jolla, Calif.; Abhijit Guha, Etobicoke, Canada; Jurgen S. Scheele, Del Mar, Calif.; Anthony J. Pawson, Toronto, Canada

[73] Assignees: Mount Sinai Hospital Corporation, Toronto, Canada; The Regents of the University of California, Oakland, Calif.

[21] Appl. No.: 593,614

[22] Filed: Jan. 30, 1996

[51] Int. Cl.$^6$ .................. C07K 1/00; C12Q 1/00
[52] U.S. Cl. ............... 435/4; 530/388.1; 530/389.1; 530/412; 435/7.1
[58] Field of Search ..................... 530/388.1, 412, 530/350; 435/7.1, 4

[56] References Cited

U.S. PATENT DOCUMENTS 5,539,096  7/1996  Babai et al. ................. 536/24.3

OTHER PUBLICATIONS

Barbarcid, Mariano, "ras Genes", Ann. Rev. Biochem., 56:779–827, (1987).
Basu, T.N., et al., "Aberrant regulation of ras proteins in malignant tumour cells from type 1 neurofibromatosis patients", Letters to Nature, 356:713–715, (Apr. 23, 1992).
Bokoch, G.M., et al., "Emerging concepts in the Ras superfamily of GTP–binding proteins", FASEB J.,7:750–759, (Jun. 1993).
Bos, J.L., "The ras gene family and human carcinogenesis", Mutat. Res., 195:255–271, (1988).
Bos, J.L., "ras Oncogenes in Human Cancer: A Review", Cancer Research, 49:4682–4689, (Sep. 1, 1989).
Chant, J., et al., "GTPase Cascades Choreographing Cellular Behavior: Movement, Morphogenesis, and More", Cell, 81:1–4, (Apr. 7, 1995).
DeClue, J.E., et al., "Abnormal Regulation of Mammalian p21$^{ras}$ Contributes to Malignant Tumor Growth in von Recklinghausen (Type 1) Neurofibromatosis", Cell, 69:265–273, (Apr. 17, 1992).
Furth, M.E., et al., "Monoclonal Antibodies to the p21 Products of the Transforming Gene of Harvey Murine Sarcoma Virus and of the Cellular ras Gene Family", Journal of Virology, vol. 43, No. 1, 294–304, (Jul. 1982).
Gibbs, J.B., et al., Identification of Guanine Nucleotides Bound to ras–encoded Proteins in Growing Yeast Cells, The Journal of Biological Chemistry, vol. 262, No. 22, 10426–10429, (Aug. 5, 1987).
Gibbs, J.B., et al., "Modulation of Guanine Nucleotides Bound to Ras in NIH3T3 Cells by Oncogenes Factors, and the GTPase Activating Protein (GAP)", The Journal of Biological Chemistry, Vo. 265, No. 33, 20437–20442, (Nov. 25, 1990).

Hattori, S., et al., "Neutralizing Monoclonal Antibody against ras Oncogene Product p21 Which Impairs Guanine Nucleotide Exchange", Molecular and Cellular Biology, vol. 7, No. 5, 1999–2002, (May 1987).
Marshall, C.J., et al., "How does p21$^{ras}$ transform cells?", Trends in Genetics, 1:91–95 (Mar. 1991).
Nanberg, E., et al., "Platelet–derived Growth Factor Increases the Turnover of GTP/GDP on Ras in Permeabilized Fibroblasts", The Journal of Biological Chemistry, vol. 268, No. 24, 18187–18194, (1993).
Feuerstein, J., et al., "Preparation and Characterization of Nucleotide–free and Metal Ion–free p21 Apoprotein", The Journal of Biological Chemistry, vol. 262, No. 18, 8455–8458, (Jun. 25, 1987).
Polakis, P., et al., "Structural Requirements for the Interaction of p21$^{ras}$ with GAP, Exchange Factors, and Its Biological Effector Target", The Journal of Biological Chemistry, vol. 268, No. 13, 9157–9160, (1993).
Santos, E., et al., "Structural and functional properties of ras proteins", FASEB J., 3:2151–2163, (Aug. 1989).
Satoh, T., et al., "Analysis of guanine nucleotide bound to ras protein in PC12 cells", FEBS, vol. 236, vol. 1, 185–189, (Aug. 1988).
Satoh, T., et al., "Accumulation of p21$^{ras}$ GTP in response to stimulation with epidermal growth factor and oncogene products with tyrosine kinase activity", Proc. Natl. Acad. Sci. USA, 87:7926–7929, (Oct. 1990).
Satoh, T., et al., "Platelet–derived growth factor stimulates formation of active p21$^{ras}$ GTP complex in Swiss mouse 3T3 cells", Proc. Natl. Acad. Sci. USA, 87:5993–5997, (Aug. 1990).

(List continued on next page.)

Primary Examiner—Lila Felsee
Assistant Examiner—Susan Ungar
Attorney, Agent, or Firm—Karl Bozicevic, Esq.; Bozicevic & Reed LLP

[57] ABSTRACT

The invention features methods for measuring the total amounts of G protein-bound GDP and GTP in mammalian cells and tissue. The method of the invention is advantageous over conventional methods in that the cells need not be exposed to phosphate-free growth conditions, which can adversely affect the accuracy of the GTP determination. Moreover, the method does not require exposure of the cells to radiolabelled phosphate in the growth medium. Standardized amounts of G protein-bound GDP and GTP are determined relative to non-nuclear cellular protein content or cellular DNA content, allowing comparison of results across different cell types. The method is particularly applicable to the detection of Ras protein bound GTP and GDP. The determination of Ras-bound GTP levels by the method of the invention provides a sensitive and accurate means of evaluating the role of Ras activation in cellular processes, such as cell proliferative disease, hormonal secretion, cellular differentiation, programmed cell death, cell cycle regulation, and protein trafficking. Treatment of abnormal processes can then more accurately targeted to the alteration of G protein activation.

13 Claims, 2 Drawing Sheets

OTHER PUBLICATIONS

Scheele, J.S., et al., "Determination of absolute amounts of GDP and GTP bound to Ras in mammalian cells: Comparison of parental and Ras–overproducing NIH 3T3 fibroblasts", *Proc. Natl. Acad. Sci. USA*, 92:1097–1100, (Feb. 1995).

Slamon, D.J., et al., "Studies of the HER–2/neu Proto–oncogene in Human Breast and Ovarian Cancer", *Science*, 244:707–712, (May 1989).

Torti, M., et al., "Erythropoietin Induces $p21^{ras}$ Activation and p120GAP Tyrosine Phosphorylation in Human Erythroleukemia Cells", *The Journal of Biological Chemistry*, vol. 267, No. 12, 8293–8298, (Apr. 25, 1992).

Grunicke & Maley (Critical Rev. In Onco, 4:389–401, 1993).

Neer (Protein Science 3:3–14, 1994).

Linder et al, (JBC, 265:8243–8254, 1990).

Johnson et al (J. Cell Biochem, 47:136–146, 1991).

Carty et al (JBS, 265:6268–6271).

METHOD OF QUANTITATING GTP AND GDP BOUND TO A G PROTEIN AND USES THEREOF

STATEMENT AS TO FEDERALLY SPONSORED RESEARCH

This invention was made with Government support under Grant No. R01-GM49360, awarded by the National Institutes of Health. The Government has certain rights in this invention.

FIELD OF THE INVENTION

The field of the invention relates to assay methods for determining activation levels of G proteins in mammalian cells, G proteins whose activation affects disease, and Ras; assay methods for quantitating the amount of GDP and GTP bound to a G protein; and screening methods.

INTRODUCTION

Ras is a member of a family of guanine nucleotide-binding proteins involved in cell signalling mechanisms. Ras activation is implicated in various cell proliferative diseases such as cancers, and other diseases where regulation of Ras activity plays a role in the development of disease. Such diseases include, but are not limited to leukemia, cancers of the breast, bladder, pancreas, lung, colon, and ovaries, and neurofibromatosis (see, for example, Barbacid, M. (1987) Ann. Rev. Biochem. 56:779–827; Bos, J. L. (1988) Mutat. Res., 195:255–271; and Bos, J. L. (1989) 49:4682–4689). Guanine nucleotide-binding proteins (G proteins), such as those in the ras superfamily, cycle between an inactive GDP-bound state and an active GTP-bound state (Santos, E. and Nebreda, A. R. (1989) FASEB J. 3:2151–2163; Preissmuth, M., Casey, et al. (1989) FASEB J. 3:2125–2131). Ras, a well studied and characteristic member of the G protein superfamily, is bound to GTP in its active state (Ras.GTP) through activation by interaction with guanine nucleotide exchange factors. Ras.GTP is converted to the inactivated GDP-bound state (Ras.GDP) through inactivation by its low intrinsic GTPase activity and by interaction with GTPase Activating Proteins (GAPs), via their GAP Related Domains (GRD) (Osterop, A. P. R. M. et al. (1992) J. Biol. Chem. 267:14647–14653; Torti, M. et al. (1992) J. Biol. Chem. 267:8293–8298; Park, S. et al. (1992) J. Biol. Chem. 265:17194–17200; Nanberg, E. and Westermark, B. (1993) J. Biol. Chem. 168:18187–18194). In mammalian cells, p120-GAP and neurofibromin (the protein encoded by the neurofibromatosis-1 gene (NF1)), are the major GAPs associated with inactivation of Ras.GTP.

Negative regulation of Ras is biologically important, as approximately 30% of human solid tumors have a mutant Ras protein which is resistant to inactivation by GAPs and, thus, remains in the activated state causing abnormally high cell proliferation (Marshall C., (1991) Trends in Genetics 7:91–95; Trahey M. and McCormick F., (1987) Science 238:542–545; Bos J. L. et al. (1989) Cancer Research 49:4682–4689). Furthermore, it is likely that mutations which decrease levels of GAP activity, such as those in patients with neurofibromatosis-1, will also lead to elevated cellular Ras.GTP levels and contribute to tumor formation as mutations in the NF1 gene is the most common known germline alteration predisposing to human neoplasia.

SUMMARY OF THE INVENTION

A method is provided for measuring standardized amounts of GDP and GTP bound to a G protein such as Ras, which method is performed on a tissue sample or on cells grown in culture medium that need not be phosphate-free. The method further provides that the cultured cells or tissue sample cells are not exposed to radiolabelled orthophosphate prior to cell lysis. The amounts of G protein-bound GTP and GDP are standardized relative to cellular DNA content or non-nuclear protein content. This method allows comparison of the standardized amount of G protein-bound GTP (such as Ras.GTP) and G protein-bound GDP (such as Ras.GDP) between different cell types. The quantitative determination of the standardized amounts of G protein-bound GTP and G protein-bound GDP in cells of tissue exhibiting G protein-activation-associated phenotype relative to cells of normal tissue is important for evaluating how to treat the tissue to alleviate disease.

Prior to the disclosure provided herein, methods of measuring Ras.GDP and Ras.GTP were applicable only to cells grown in culture and required exposing the cultured cells to phosphate-free medium for radiolabelling with $^{32}PO_4$. Previous methods requiring cell culturing were not applicable to tissue samples or cells that could not be grown in culture. The present method is carried out without the need for culturing cells in radioactive medium, a process that requires large amounts of radioactive material, the purchase and disposal of which is very expensive. Additionally culturing cells in a phosphate-free medium results in low intracellular concentrations of phosphorylated intermediates inside the cell, including ATP, ADP, GTP, GDP, phosphorylated glucose, and the like. A reduced ATP concentration can lead to anomalous results in Ras.GTP levels, thereby eliminating the ability to accurately determine the amount of GTP and GDP bound to Ras under normal physiological conditions.

The presently disclosed methods allow determination of G protein-bound guanine nucleotides, such as Ras.GTP and Ras.GDP, in tissue samples and use of that information to determine G protein activation affecting cellular physiology, such as hormonal secretion, cellular differentiation, programmed cell death, intracellular protein trafficking, regulation of cell cycle and abnormally high cell proliferation (see, for example, Bokoch, G. M. and Der, C. J. (1993) FASEB J. 7:750–759; Chant, J. and Stowers, L. (1995) Cell 81:1–4; Grand, R. J. A. and Owen, D. (1991) Biochem. J. 279:609–631; and Barbacid, M. (1987) Ann. Rev. Biochem 56:779–827). The method of the invention provides that cultured cells need not be maintained in phosphate free culture medium prior to assay for G protein-bound GTP and G protein-bound GDP. The method also includes the determination of GDP- and GTP-bound G protein as a function of non-nuclear cellular protein content or cellular DNA content of the G-protein sample as a means of comparing guanine nucleotide-bound G protein levels between cultured cell or tissue samples.

In one aspect, the invention provides an assay method for determining the amount of G protein-bound GTP in a cell of a mammal. According to the invention, a sample of test cells is obtained which cells have not been exposed to phosphate-free growth conditions so as not to alter the concentration of phosphorylated intermediates within the cells. In addition, it is not necessary to the invention to expose the cells to radiolabelled orthophosphate as required by the $^{32}PO_4$ incorporation method. The G protein of interest is isolated from a lysate of the cells to provide a G protein sample. G protein-bound guanine nucleotide is eluted from the isolated G protein to provide eluted GTP and eluted GDP. The eluted GTP is converted to ATP and the amount of ATP in the G protein sample is determined. The amount of ATP is a measure of the amount of G protein-bound GTP present in the cells. The amount of G protein-bound GTP is a measure of the activation state of the G protein.

In one embodiment of the invention, the eluted GTP is converted to ATP by nucleotide diphosphate kinase (NDP kinase) followed by reaction with luciferase to produce detectable light emission in proportion to the amount of GTP eluted from the G protein.

In another embodiment of the invention, the amount of G protein-bound GTP in a sample of test cells is compared with the amount of G protein-bound GTP determined for a control sample of normal cells. By comparing the amount of G protein-bound GTP between test cells and normal control cells and determining a difference, a probability of G-protein activation is deduced.

In yet another embodiment of the invention, the amount of G protein-bound guanine nucleotide, such as GTP and/or GDP is determined relative to a standardization function. A sample standardization function according to the invention may be the non-nuclear protein content of the cells, the cellular DNA content of the cells, or the like. The amount of G protein-bound GTP (measured as GTP-converted ATP) is calculated with respect to the selected standardization function to provide a standardized amount of G protein-bound GTP in a sample of cells. The standardized amount of G protein-bound GTP in test and normal control samples is compared and a probability of G protein activation in the test cells is deduced. In a preferred embodiment of the invention, the amount of standardized G protein-bound GTP in a sample of test cells is at least approximately 2-fold higher than the amount of standardized G protein-bound GTP in a sample of normal cells assayed as a control.

In still another embodiment of the invention, the G protein is any G protein which can be isolated from a cell sample with a guanine nucleotide bound to the G protein as it occurs in the cell. Preferably, the G protein of interest is isolated by immunoprecipitation. Also, the G protein is preferably Ras. According to one embodiment of the invention, Ras is immunoprecipitated from a lysed cell sample of test cells or control cells using the antibody Y13-259.

In another embodiment of the invention, eluted GDP is converted to detectable GTP. Preferably, eluted GDP is converted to detectable GTP using $\gamma$-$^{32}PO_4$ and NDP kinase. The amount of detectable GTP is determined and quantitated with respect to the value of the standardization function, such as the non-nuclear protein content of the cell sample, or the DNA content of the cell sample, thus providing the standardized amount of G protein-bound GDP for a test or control cell sample. The standardized amount of G protein-bound GDP and G protein-bound GTP are compared for a test and control sample. The probability of G protein activation is deduced based on the relative values of the standardized amount of G protein-bound GTP determined for the control cells and test cells, as well as the standardized amount of G protein-bound GDP determined for the control cells and test cells. Preferably, the standardized amount of G protein-bound GTP is at least approximately 2-fold higher in the test cell sample than in the control cell sample.

In yet another preferred embodiment of the invention, the cell sample is a tissue sample of a mammal such as a human patient. Preferably, the tissue sample is extracted directly from the mammal and the cells of the tissue are not grown in phosphate-free medium, or exposed to radiolabelled orthophosphate prior to isolation of the G protein of interest. Preferably, at least approximately 5–10 million cells are assayed. It is preferred that the test tissue sample is taken from tissue suspected of containing cells which are exhibiting a phenotype associated with abnormal G protein activation such as, but not limited to, proliferation at an abnormally high rate relative to normal cells, altered hormonal secretion, abnormal cellular differentiation, altered cell cycle regulation, abnormal intracellular protein trafficking, altered programmed cell death. A control sample of normal cells or tissue is cells or tissue known to be free of cells which are exhibiting a phenotype associated with abnormal G protein activation.

The method of the invention has broad applications as it can be utilized to study tissues where Ras or other G proteins are implicated to play a pathogenic role.

An aspect of the invention is a method of diagnosing abnormally high cell proliferation in a population of cells, such as a tissue sample, by determining the amount of G protein-bound GTP and, optionally, G protein-bound GDP, in the tissue sample. Preferably, the G protein is Ras. The diagnostic method of the invention provides that a test tissue is deduced to be exhibiting abnormally high cell proliferation (e.g., is cancerous) if the test tissue has an increase in Ras-bound GTP of at least approximately 2-fold relative to a sample of normal tissue. Preferably, the tissue sample is from an organism in which G protein activation is implicated in altered cellular function. Such organisms include, but are not limited to, a mammal or a human patient.

An advantage of the invention is the ability to demonstrate abnormal G protein activation in a tissue sample which is made up partially of normal tissue as well as tissue exhibiting abnormal G protein activation. Increased sensitivity and accuracy is required in order to compare amounts of standardized G protein-bound GTP, preferably Ras-bound GTP and Ras-bound GDP, between normal and test tissue. The method of the invention provides the sensitivity and accuracy necessary for such comparison, and thus fills a currently unmet need in the field of G protein activation analysis in cells and tissue.

The method of the invention provides the advantage that cultured cells are maintained in media having physiological concentrations of phosphate (i.e. media are not phosphate-free), thus preventing aberrant changes in G protein-bound GTP caused by the assay methodology itself and unrelated to the actual functioning of G proteins and their accessory proteins. Tissue samples tested by the method of the invention are not exposed to phosphate-free media prior to the desired dissociation of guanine nucleotides from the G protein for the purpose of detection and quantitation. As a result, the invention disclosed herein provides superior sensitivity and accuracy of the amount of G protein-bound GTP and G protein-bound GDP in a cultured cell and, for the first time, the ability to measure G-protein-bound GTP and GDP levels in a tissue sample for determination of abnormal G protein activation.

The method provides an advantage by making it unnecessary to incubate test and control cells in culture medium containing radiolabelled orthophosphate since, according to the invention, the guanine nucleotides are converted to detectable compounds subsequent to isolation of the G protein-quanine nucleotide complexes. Thus, the method of the invention exposes the user to far lower amounts of radioactivity and reduces the expense of purchasing and disposing of radioactive material.

The method of the invention provides another advantage by being useful for analyzing G protein-bound GTP in a tissue sample which samples cannot be labelled by growth in the presence of radioactive orthophosphate. Thus, by discovering an accurate and sensitive alternative to $^{32}PO_4$- incorporation methods, the applicants provide a useful method of diagnosing Ras-related cell proliferation (or other G protein-related cell disease) in a tissue sample of a mammal, such as a human patient.

By "standardized amount of G protein-bound GTP" or "standardized amount of G protein-bound GDP" is meant the quantitation by the method of the invention of the guanine nucleotides bound to a G protein, independent of the guanine nucleotides present in the unbound state or bound to other proteins. The standardized amount of G protein bound-guanine nucleotide is determined and reported relative to the amount of non-nuclear protein in the sample or the cellular DNA content of the sample. The same quantitation defines the terms "standardized amount of Ras-bound GTP or GDP" where the G protein is Ras.

By "abnormal G protein activation phenotype" is meant a phenotype of a test cell population characterized as abnormally high cell proliferation (i.e., increased cell growth) above the rate of cell growth of a control population such that cell growth is 20% above, preferably 50% above, or more preferably greater than 100% above the growth of a control population. For example, abnormally high proliferating cells may be considered to be cancerous cells of a tumor. Other phenotypes associated with abnormal G protein activation included, but are not limited to, altered hormonal secretion, abnormal cellular differentiation, altered cell cycle regulation, abnormal intracellular protein trafficking, and altered programmed cell death.

These and other objects, advantages and features of the present invention will become apparent to those persons skilled in the art upon reading the details of the methods and usage as more fully set forth below.

DETAILED DESCRIPTION

Figure 1:
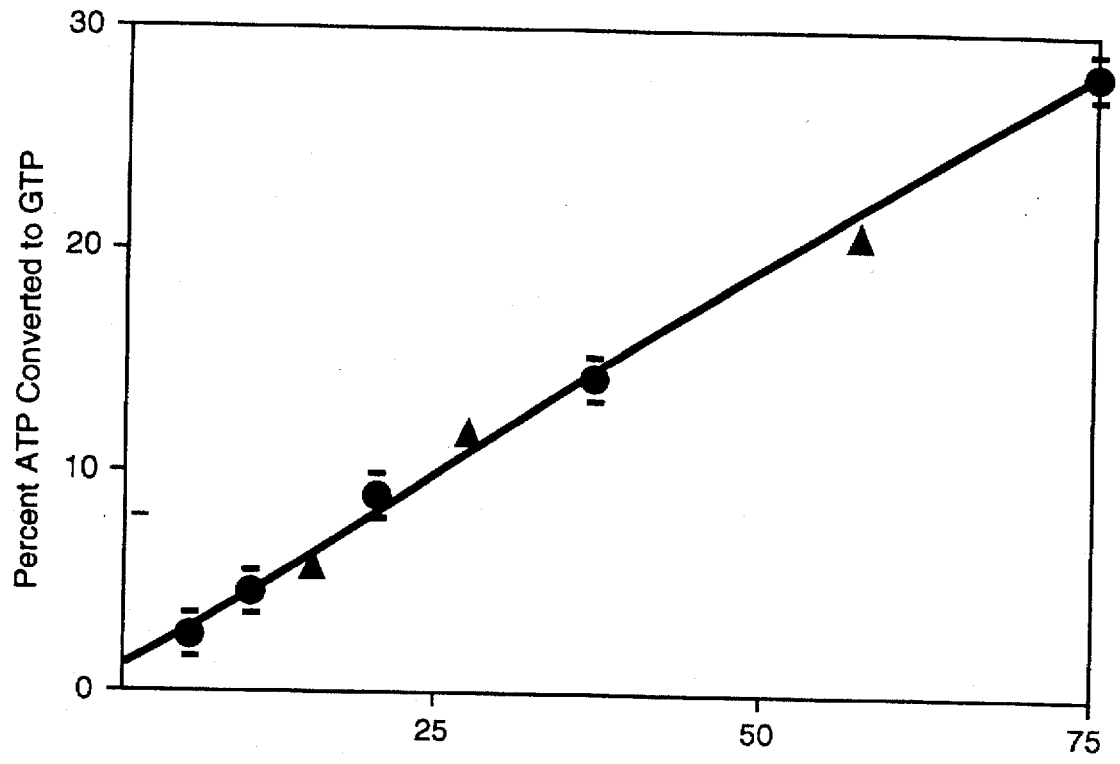
FIG. 1 is a graphical representation of the measurement of GDP eluted from a G protein of interest (Ras) using ATP and NDP kinase. The percent of [γ-$^{32}$P]ATP converted to [γ-$^{32}$P]GTP is plotted versus the fmol of GDP in standards.

Before the present methods of measuring G protein-bound guanine nucleotides in cells and tissue are described, it is to be understood that this invention is not limited to the particular G protein or methods described as such G proteins and methods may, of course, vary. It is also to be understood that the terminology used herein is for the purpose of describing particular embodiments only, and is not intended to be limiting since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited.

Increased levels of Ras-bound GTP have been found in cell lines exhibiting abnormally high levels of cell proliferation. For example, elevated Ras.GTP levels have been demonstrated in neurogenic sarcoma cell lines from NF1-deficient patients, which cell lines do not express neurofibromin but have normal levels of p120-GAP (DeClue J. et al., (1992) Cell 69:265–273; Basu T. et al., (1992) Nature 356:713–715). The role of NF1 as a negative regulator of Ras was demonstrated when in vitro proliferation of neurogenic sarcoma cells from NF1-deficient human patients was inhibited by transfection of the GAP related domain portion of neurofibromin, thereby restoring GAP function. In addition, proliferation of the sarcoma cell line was also inhibited if the sarcoma cells were microinjected with neutralizing Ras antibodies (DeClue J. et al., (1992) Cell 69:265–273; Basu T. et al., (1992) Nature 356:713–715).

The method of the invention provides that G protein-bound guanine nucleotide measurements are standardized to non-nuclear cellular protein content or cellular DNA content. Such measurements offer an advantage since the invention uniquely provides that an increase in the standardized amount of activated G protein is discernable and comparable between cell populations. As shown in Table I, LTR-cHa-ras (N) (cells transformed with wild-type cHa-ras) contain markedly increased amounts of total Ras (Ras.GTP+ Ras.GDP) but similar levels of activation (%GTP/(GDP+ GTP) relative to parental, untransformed cells. Interestingly, cells transformed with LTR -cHa-ras (A) (activated Ras) had similar total amounts of Ras as cells transformed with LTR-cHa-ras (N). However, the former cells had a much greater amount of Ras in the active GTP-bound state. The ability to measure the total amount of Ras in a sample and to compare measurements between different cell types is a unique advantage of the invention.

A $^{32}$PO$_4$-incorporation method developed by Satoh, et al. (Satoh, T. et al (1990) Proc. Nat. Acad. Sci. USA 87:5993–5997; Satoh, T. et al. (1990) Proc. Nat. Acad. Sci. USA 87:7926–7929) for the determination of Ras-bound GTP had the disadvantage that the procedure itself adversely affected the accuracy of the method. In the Satoh method, the percentage of Ras proteins in the GDP and GTP bound states was determined by incubating cells with $^{32}$PO$_4$ to radiolabel the intracellular GDP and GTP pools and, therefore, the GDP and GTP bound to Ras (Satoh, T. et al. (1988) FEBS Letters 236:185–189; Satch, T. et al. (1990) Proc. Natl. Acad. Sci. USA 87:7926–7929; Gibbs, J. B. et al. (1987) J. Biol. Chem. 262:10426–10429). Ras was first immunoprecipitated from cell extracts and the bound, labeled GDP and GTP were eluted and separated by thin layer chromatography (TLC). As generally applied, this $^{32}$PO$_4$-incorporation method measured only the relative amounts of each guanine nucleotide bound to Ras without standardization of the bound GTP and GDP to a cellular standardization function. Additionally, it required that cells be incubated for several hours in phosphate-free medium which markedly decreases the intracellular concentration of phosphorylated intermediates and, as demonstrated herein, can adversely affect the accuracy of the method by changing the amount of Ras-bound GTP.

EXAMPLES

The following examples are presented so as to provide those of ordinary skill in the art with a complete disclosure and description of how to use the methods of the invention and are not intended to limit the scope of what the inventors regard as their invention. Efforts have been made to insure accuracy with respect to numbers used (e.g. amounts, temperature, etc.) but some experimental errors and deviation should be accounted for. Unless indicated otherwise, parts are parts by weight, temperature is in degrees C., and pressure is at or near atmospheric.

There now follows a description of the methods for determining the amounts of Ras-bound GTP and Ras-bound GDP in a mammalian cell or tissue sample, for the determination of G protein activation. The examples below are provided for the purpose of illustrating the invention, and should not be construed as limiting. While the examples relate to the G protein, Ras, the methods are useful for the determination of any G protein which can be isolated in the GTP- and GDP-bound state using an appropriate antibody raised to that G-protein.

Example 1

General Procedures

Cell Culture

NIH3T3 cells were grown in Dulbecco's modified Eagle's medium (DMEM) supplemented with 10% transferrin-enriched calf serum (ECS) and were harvested at confluence by washing the cells once with ice-cold phosphate-buffered saline and scraping the cells off the plate with a rubber policeman. Cultured test cells (for example, HL-60 cells) were grown in RPMI 1640 medium supplemented with 10% ECS and were harvested at end log phase by centrifugation. Cell culture according to the method of the invention includes culture medium that contains standard physiological concentrations of phosphate and which is not phosphate-free. Preferably, the culture medium contains approximately at least 1 mM phosphate.

Tissue Specimens Preparation

Tissue specimens from human patients were sectioned, inserted into cryo-vials and flash frozen in liquid nitrogen, preferably within 30 seconds of extraction from the patient, in accordance with the University of Toronto human ethics committee guidelines. Two neurogenic sarcomas (two measurements on different portions of one tumor, and three measurements from a second tumor), four neurofibromas from different NF1-deficient patients, and four schwannoma specimens obtained from non-NF1 patients were examined. Two cryo-vials from each tumor, each containing approximately 1 cm$^3$ of specimen, were used for the Ras assay. An additional cryo-vial was used to extract total RNA for RT-PCR (Reverse Transcriptase Polymerase Chain Reaction). Formalin-fixed sections used for neuropathological diagnosis of the tumors were utilized for neurofibromin immunohistochemistry. Ras-bound GTP levels were measured in RT8 cells (v-Ha-ras transformed fibroblasts, a gift from Dr. J. Stone, Jackson Laboratory, Maine, USA) in each experiment as positive controls.

Example 2

Determination of Ras-bound GTP and Ras-bound GDP in Cells Cultured in Vitro Immunoprecipitation of Ras Proteins and Elution of GTP and GDP From Ras Harvested cells were resuspended at a density of 50×10$^6$ cells/ml in 50 mM Hepes, pH 7.4, 10 mM MgCl$_2$, 150 mM NaCl, 1% nonidet P-40, 0.5 mM phenylmethylsulfonylfluoride and 10 µg/ml of aproprotinin, leupeptin and pepstatin (extract buffer) (Satoh, T. et al. (1988) FEBS Letters 236:185–189; Gibbs, J. B. et al. (1990) J. Biol. Chem. 265:20437–20442). After gentle shaking for 10 min at 4° C., the lysed cells were centrifuged at 11,000×g for 10 min and supernatants were applied to 0.6×7.5 cm Sephadex G25 (Pharmacia) columns equilibrated in extract buffer. Protein-containing fractions were pooled and NaCl, SDS and deoxycholate were added to final concentrations of 500 mM, 0.05% and 0.5%, respectively. The samples were divided in half and either 3 µg of the anti-Ras antibody Y13-259 (experimental sample, Furth, M. E. et al. (1982) J. Virology 43:294–304) or 3 µg of rat IgG (blank sample) were added. To both samples 30 µg of goat anti-rat IgG (CalBiochem, San Diego, Calif.) and 15 µl of protein-G agarose (CalBiochem) were also added. The sample tubes were rotated gently for 16 h at 4° C. and centrifuged at 11,000×g for 20 sec. Protein was measured in the supernatants by the Bradford method (Bradford, M. M. (1976) Anal. Biochem. 72:248–254) and the pellets containing the immunoprecipitate were washed eight times with 50 mM Tris-HCl, pH 7.4, 10 mM MgCl$_2$, 500 mM NaCl, 0.1% Triton X-100, 0.005% SDS and three times with 20 mM Tris-PO$_4$, pH 7.8. After the last wash, the immunoprecipitates were resuspended in 30 µl of a solution of 5 mM Tris-PO$_4$, pH 7.4, 2 mM DTT, 2 mM EDTA and heated at 100° C. for 3 min; the samples were cooled on ice and centrifuged at 11,000×g for 5 min.

The primary antibody, Y13-259 (Furth, M. E. et al. (1982) supra), was preferably incubated overnight with the cell extracts to quantitatively immunoprecipitate Ras (Nanberg, E. and Westermark, B. (1993) J. Biol. Chem. 168:18187–18194) under conditions which inhibit the conversion of Ras-bound GTP to Ras-bound GDP and also inhibit dissociation of guanine nucleotides from Ras. At 4° C. the rate of dissociation of GDP and GTP from Ras is extremely slow in the presence of Mg$^{++}$ and Y13-259, while high salt concentrations inhibit GAP activity (Torti, M., et al. (1992) J. Biol. Chem. 267:8293–8298; Peuerstein, J. et al. (1987) J. Biol. Chem. 262:8455–8458; Hattori, S. et al. (1987) Mol. Cell. Biol. 7:1999–2002). Heating the immunoprecipitates at 100° C. for 3 min quantitatively eluted GTP and GDP from Ras and destroyed less than 5% of the GDP and GTP. GDP and GTP were measured in the immunoprecipitate supernatants as described below.

Measurement of GDP Using NDP Kinase

Ras-bound GDP was measured using the same procedure for cell culture samples and tumor specimen.

GDP was measured by conversion to [γ-$^{32}$P]GTP using NDP kinase (nucleoside diphosphate kinase) and [γ-$^{32}$P] ATP:

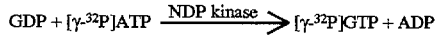

The reaction mixture contained, in a final volume of 10 µl, 500 pmol Tris-HCl, pH 7.4, 100 pmol MgCl$_2$, 250 fmol ATP, 2.5 milliunits NDP kinase, 0.01 µCi [γ-$^{32}$P]ATP and either 5 µl of sample (supernatant containing eluted GDP) or 5–100 fmol of GDP standard. Preferably, conversion of GDP to GTP was performed by incubating the reaction mixture for 90 min at 37° C. [γ-$^{32}$P]GTP was separated from excess [γ-$^{32}$P]ATP by TLC on plastic-backed cellulose plates developed for 8 h in saturated ammonium sulfate/water/3M sodium acetate, pH 5.5/10N sodium hydroxide/isopropanol (80/10/6/2/2). The areas corresponding to GTP and ATP were identified either by nonradioactive markers visualized under ultraviolet light or by exposing the TLC plates to X-ray film. The separated radiolabelled GTP and ATP spots were cut out and radioactivity was quantitated by liquid scintillation counting. The ratio of radioactivity incorporated into GTP over that in [ATP+GTP] was used to calculate a conversion factor to correct for possible errors incurred during spotting the TLC plates.

GDP measurements were linear over a range from 5–75 fmol (FIG. 1, filled circles); higher amounts of GDP could be measured by increasing the amount of ATP in the incubation mixture. When the amount of Ras-bound GDP was measured in NIH3T3 cells (control), it increased linearly with the number of cells extracted (over a range from 0.5, 1, and $2 \times 10^6$ cells (FIG. 1, filled triangles) yielding 33 fmol/$10^6$ cells. Each data point of FIG. 1 is the mean±SD of three independent experiments performed in duplicate. When the data were expressed per milligram of non-nuclear cellular protein, NIH3T3 cells (control) and HL-60 cells (Ras-transformed cells) were found to contain approximately the same amount of Ras-bound GDP (509±74 and 615±95 fmol/mg protein, respectively; Table I).

TABLE I

Ras-bound GDP and GTP in NIH3T3 and HL-60 cells

| Cell type | GDP | GTP | GTP/ (GDP + GTP) |
|---|---|---|---|
| | fmol/mg of protein | | % |
| Parental NIH3T3 cells | 509 ± 74 | 1.3 ± 0.3 | 0.25 |
| LTR-cHa-ras(N) | 7008 ± 825 | 21.3 ± 7.1 | 0.30 |
| LTR-cHa-ras(A) | 5013 ± 613 | 2049 ± 332 | 29 |
| HL-60 cells | 615 ± 95 | 58 ± 7.1 | 8.6 |

NIH3T3 fibroblasts were grown to confluence, harvested, and lysed as described herein. LTR-cHa-ras(Nonactivated) and LTR-cHa-ras(Activated) cells are stable transfectants of NIH3T3 cells overexpressing wild-type and activated Ha-ras, respectively, under control of the murine mammary tumor virus promoter (Schonthal, A. et al. (1988) Cell 54:325–334). The cells were treated with 1 μM dexamethasone for 24 hr prior to harvesting.
GDP and GTP were measured by the method of the invention. The data are expressed as fmol of guanine nucleotide per milligram of cellular protein and are the means ±S.D. of at least three independent experiments performed in duplicate.

NIH3T3 cells overexpressing wild-type Ha-ras contained 7008±825 fmol of Ras-bound GDP per mg of protein or about 14 times more Ras-bound GDP than parental cells, while cells overexpressing activated Ha-ras contained about 10 times more Ras-bound GDP than parental cells (Table 1).

Measurement of GTP Using NDP Kinase and Luciferase

Ras-bound GTP was measured using the same procedure for cell culture samples and tumor specimen.

Eluted GTP was converted to ATP in the presence of ADP and NDP kinase; ATP was measured using luciferase and luciferin (Lemasters, J. J. and Hackenbrock, C. R. (1978) Methods Enzymol. 57:36–50; Scheele, J. S., et al. (1994), Proc. Natl.Acad. Sci. USA, 92:1097–1100).

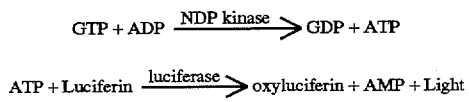

The reaction mixture contained, in a final volume of 15 μl, 1.5 μmol glycine, pH 7.8, 120 nmol MgSO$_4$, 10 nmol EDTA, 15 nmol DTT, 10 pmol ADP, 4 nmol luciferin, 2.5 milliunits NDP kinase, $8 \times 10^8$ light units of luciferase, 15 μg bovine serum albumin and either 10 μl of sample (supernatant of the immunoprecipitate) or 0.5–20 fmol of GTP standard. In replicate tubes, the NDP kinase was omitted to check for ATP contamination. The reaction was started by adding the sample to the reaction mixture. Light emission was measured over a ten minute interval using either a liquid scintillation counter or a photon counting luminometer.

The amount of GTP in the samples was obtained from a standard curve, and corrected by subtracting the GTP value obtained from the rat IgG immunoprecipitated sample from the corresponding sample immunoprecipitated with Ras-specific Y13-259 antibody. This corrected GTP value was expressed per mg protein or per μg DNA (Table 1).

Figure 2:
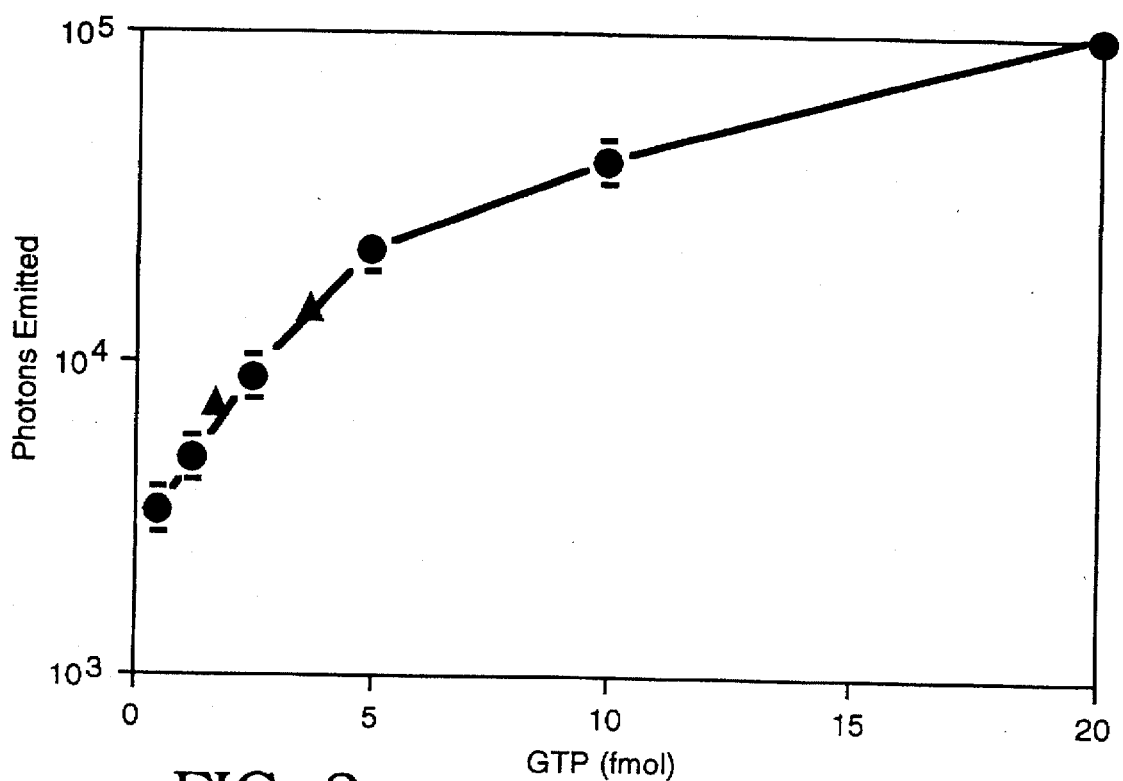
FIG. 2 is a graphical representation of the measurement of GTP eluded from a G protein of interest (Ras) using a coupled assay using NDP kinase and luciferase to convert GTP to ATP, followed by ATP driven light emission in the luciferase assay. Photons emitted were plotted versus fmol of GTP in standards.

GTP measurements were linear over a range from 0.5–5 fmol (FIG. 2, standard samples are filled circles); at higher GTP concentrations light emission no longer increased linearly, presumably because of product (oxyluciferin) inhibition of luciferase (Lemasters, J. J. and Hackenbrock, C. R. (1978) Methods Enzymol. 57:36–50). When the amount of Ras-bound GTP was measured in NIH3T3 cells, it increased linearly with increasing amounts of cells (FIG. 2, test samples are filled triangles) yielding 0.1 fmol/$10^6$ cells.

HL-60 cells express a mutated N-Ras in which the glutamine at position 61 is replaced by a leucine (Bos, J. L. et al. (1984) Nucl. Acids Res. 12:9155–9163); this change markedly decreases the intrinsic GTPase activity of Ras and GAP stimulation of Ras GTPase activity, thereby increasing the amount of GTP bound to Ras (Santos, E. and Nebreda, A. R. (1989) FASEB J. 3:2151–2163; Polakis, P. and McCormick, F. (1993) J. Biol. Chem. 268:9157–9160). Consistent with this activating mutation of N-Ras, HL-60 cells contained 58±7.1 fmol/mg protein of Ras-bound GTP or approximately 45 times as much Ras-bound GTP as NIH3T3 cells (Table 1). Thus, a transformed cell line (HL-60) is demonstrated to have higher amounts of Ras.GTP than a nontransformed cell line (NIH3T3) using the method of the invention.

Calculation of Amounts of GDP and GTP Bound to Ras

To determine the amount of GDP in a sample, the conversion factor of the blank sample was subtracted from the conversion factor of the experimental sample. Generally, for GDP the conversion factor of the blank sample was less than approximately 10% of the experimental sample. To determine the amount of GTP in a sample, light emission in the absence of NDP kinase was subtracted from light emission in the presence of NDP kinase for both the blank and experimental samples; the blank sample value was then subtracted from the experimental sample value. GTP light emission by the blank sample was less than approximately 10% of the experimental sample. The amounts of GDP and GTP in the samples were determined from standard curves and the data were expressed as fmol of GDP or GTP per $10^6$ cells, per milligram of non-nuclear cellular protein, or per μg of cellular DNA.

Example 3

Determination of Ras.GTP and Ras.GDP in Cells of a Tumor

Elution of GTP and GDP from Ras in Tumor Samples

Flash frozen tumor specimens were immersed in 2.5 ml of freshly prepared cold Ras lysis buffer (10 mM Hepes pH 7.4; 1 mM MgCl$_2$; 1 μg/ml leupeptin and aprotinin; 0.25 μg/ml pepstatin A; 150 mM NaCl; 1% NP-40; 0.5 mM PMSF) and homogenized. Preferably, all steps of the procedure, including the immunoprecipitations, prior to heat-induced elution of guanine nucleotides were performed at 4° C. From the homogenate, 100 μl was aliquoted for DNA extraction and quantitated using a standard trichloroacetic acid (TCA) precipitation procedure (Sambrook, J. et al. ed. Molecular Cloning: A Laboratory Manual, 2nd ed., Cold Spring Harbor Laboratory Press, 1989, Appendix E.18). RT8 cells (v-Ha-ras transformed fibroblasts as positive controls) were washed with cold PBS, suspended in 600 μl of PBS, centrifuged, and the pellet lysed in 200 μl of Ras lysis buffer. The homogenates were centrifuged for 30 min. at 10,000×g to remove nuclear and other cellular debris.

Following lysis of cells in a tissue sample, the procedure for measurement of G protein-bound GTP and GDP is essentially the same as for tissue culture samples. The procedure followed for the exemplified tissue samples is provided as additional guidance to one of ordinary skill in the art.

Sephadex-G25 columns (10 ml size, Pharmacia) were pre-cleared with HNMN buffer (50 mM Hepes pH 7.4; 150 mM NaCl; 10 mM $MgCl_2$; 1% NP-40). The supernatants (approximately 2.5 ml) from the tumor homogenates and from the RT8 fibroblasts were loaded onto separate columns, and protein containing fractions for each sample were isolated and pooled. To half of each pooled protein sample was added 3 μg of the monoclonal anti-(Ha, Ki, N) Ras antibody (Y13-259; Oncogene Science), and to the remaining half was added 3 μg of rat IgG. The samples were gently shaken overnight with 30 μg of goat anti-rat IgG:Fc (CalBiochem) and 30 μL of protein-G agarose beads (CalBiochem). The agarose beads were centrifuged at 11,000×g for 5 min., and the supernatant was retained for protein determination by the method of Smith, P. K. et al., Anal. Biochemistry 150:76–85 (1985). The agarose pellets were washed eight times in 1.5 ml of 50 mM Hepes pH 7.4, 10 mM $MgCl_2$, 500 mM NaCl, 0.1% Triton X-100, 0.005% SDS, three times with 20 mM Tris-$PO_4$; and once with 5 mM Tris-$PO_4$. GTP and GDP bound to Ras were eluted in 30 μl of 5 mM Tris-$PO_4$, 2 mM DTT, 2 mM EDTA by heating at 100° C. for 3 min. The eluted samples were stored at −70° C. until assay of GTP and GDP content.

Quantitation of Ras-bound GTP and GDP in Positive Control RT8 Cells

Figure 3:
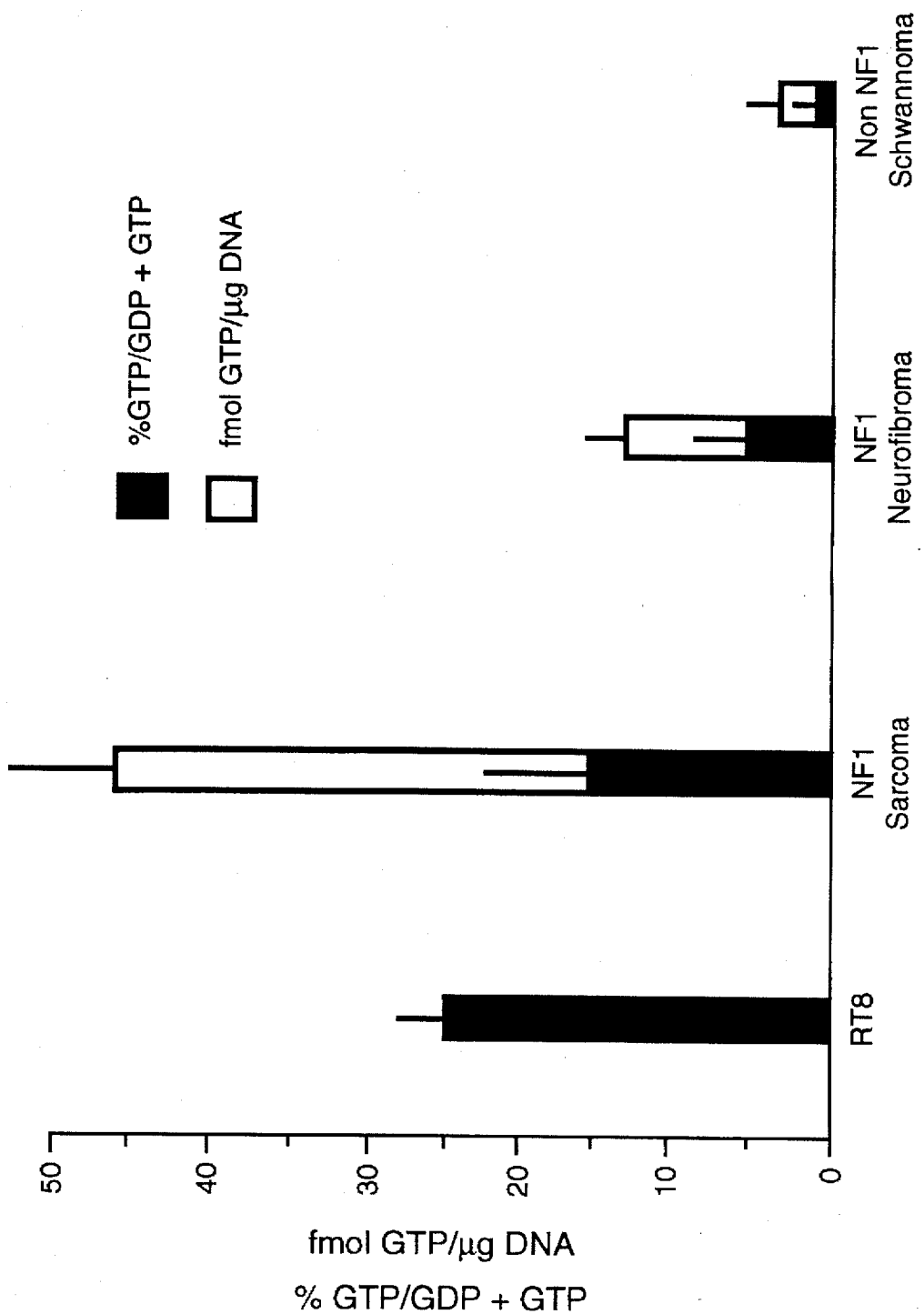
FIG. 3 is a bar graph of levels of activated Ras.GTP (mean±S.E.M.) in RT8 fibroblasts which harbor an activating mutation of ras, NF1 sarcomas (n=5), NF1 neurofibromas (n=4), and non NF1 schwannoma (n=4) tumor specimens. The Ras.GTP levels are expressed as a percentage of total Ras.GTP plus Ras.GDP (black columns) and in amounts standardized to DNA content of the tumors (white columns).

RT8 cells were analyzed along with the tumor specimens in each tissue assay experiment as a positive control. The amount of Ras bound to GTP and GDP in ras-transformed RT8 fibroblasts was 83±24 fmol/mg protein and 276±88 fmol/mg protein, respectively (Table III). Converted to percentage [GTP]/([GDP+GTP]×100), approximately 25%±3% of the total Ras was in the activated GTP bound state in these positive control cells (FIG. 3).

Quantitation of Ras-bound GDP in Tumor Tissue

GDP was measured using nucleoside diphosphate kinase (NDP kinase, Sigma, St. Louis, Mo.), which converted eluted GDP to detectably labelled GTP (Scheele J. S., et al. (1994) Proc. Natl. Acad. Sci USA 92:1097–1100). A 5 μl aliquot of eluted sample or 0–100 fmol of GDP standards were mixed with 0.01 μCi of [γ-$^{32}$P]ATP (New England Nuclear) in the presence of NDP kinase. The excess [γ-$^{32}$P]ATP was separated from the synthesized [γ-$^{32}$P]GTP by thin layer chromatography. The amount of GDP in the sample, expressed in fmol as a function of the amount of [γ-$^{32}$P]GTP produced, was obtained from a standard curve. The values obtained from the rat IgG immunoprecipitated samples (control sample) were subtracted from the corresponding samples immunoprecipitated with the Y13-259 antibody (test sample) to provide a corrected GDP value expressed per mg of non-nuclear cellular protein in non-NF1 and NF1 mutant tissues (Table 1).

Quantitation of Ras-bound GTP in Tumor Tissue

Ras-bound GTP was measured by conversion of eluted GTP to ATP and detection of ATP by a luciferase assay using the procedure described in Example 2. The results provided in Table II demonstrate that the amount of Ras-bound GTP increases at least an average of two-fold in tumor tissue relative to control tissue.

Levels of Ras.GTP in NF1 Neurogenic Sarcomas

Enough tissue was available for two experiments from patient #1 and three experiments from patient #2, both involving NF1 neurogenic sarcomas (two cryo-vials of specimen per experiment). The percentage of the total Ras that was activated ([GTP]/[GDP+GTP]×100) ranged between 7–35% (Table II) with an average value of 15.4±5.2% in the NF1 neurogenic sarcomas, when normalized against total non-nuclear cellular protein (FIG. 3).

The results of the assay for Ras.GTP in NF1 sarcoma tumor specimens were in agreement with the results for the control, cultured RT8 fibroblasts; Ras.GTP was elevated in abnormally highly proliferating cells (Table II). Levels of Ras.GTP were elevated approximately 15-fold in the NF1 sarcomas, compared with non-NF1 schwannomas. Furthermore by RT-PCR analysis of NF1 expression and immunohistochemistry of NF1 production, NF1 expression was markedly diminished in the sarcoma, with only a small amount of the type 1 NF1 isoform being detected.

Levels of Ras.GTP in Benign NF1 Neurofibromas

The enzymatic-based method of the invention provided herein, enabled a determination of Ras.GTP levels in benign NF1 neurofibromas, which do not grow in culture and therefore, cannot be analyzed by the $^{32}PO_4$-incorporation method. Compared to non-NF1 schwannomas, levels of Ras.GTP were increased approximately four-fold in these NF1 neurofibromas (Table II). Other methods of associating cellular function with cellular proliferation in NF1 deficiency-related disease have shown no difference between non-proliferative and abnormally proliferating tissue, making the method of the invention a necessary tool for Ras.GTP determination in tissue. For example, no differences in NF1 expression were detected by RT-PCR between these two tumor groups. Many different cell types are found in neurofibromas, with the actual transformed cell(s) that give rise to the tumor, presently unknown (Guha A. et al., (1995) Neurological Surgery, Fourth Edition, Philadelphia: W. B. Saunders; Peltonen J. et al., (1983) Acta Neuropathologica 61:275–282). Therefore, the NF1 expression determined by RT-PCR may reflect fibroblasts or other non-transformed cells associated with the neurofibromas, rather than the actual tumor cells. In addition, despite abundant NF1 expression demonstrated by RT-PCR, point mutations leading to decreased functional neurofibromin and hence increased Ras.GTP levels in the neurofibromas, may also be present. Immunohistochemistry was unable to prove or disprove this hypothesis conclusively. Less overall neurofibromin staining was observed in the neurofibromas compared to the non-NF1 schwannomas. However, the neurofibromas had a more myxoid acellular background compared to the schwannomas. Although most of the cells expressed neurofibromin as seen by immunohistochemistry, the non-expressing cells are likely to be the transformed cells that form the neurofibromas and contribute to the elevated levels of activated Ras.GTP.

TABLE II

Ras.GTP levels in human peripheral nerve tumors

| Sample | | Patient # | GDP (fmol/mg protein) | GTP | % [GTP]/[GDP+GTP] | GTP fmol/μg DNA |
|---|---|---|---|---|---|---|
| RT8 v-ras transformed | | | 276 ± 88 | 83 ± 24 | 25 ± 3 | |
| NF1 | sarcoma | 1 | 114 | 9 | 7 | |
| | | 1 | 90 | 10 | 10 | 61 |
| | | 2 | 84 | 17 | 17 | 33 |
| | | 2 | 47 | 4 | 8 | 55 |
| | | 2 | 113 | 61 | 35 | 35 |
| NF1 | neuro-fibroma | 1 | 409 | 13 | 3 | 8 |
| | | 2 | 211 | 18 | 8 | 11 |
| | | 3 | 561 | 6 | 1 | 14 |
| | | 4 | 198 | 27 | 12 | 20 |
| Non NF1 | schwan-noma | 1 | 412 | 5 | 1 | 4 |
| | | 2 | 291 | 4 | 1 | 2 |
| | | 3 | 547 | 5 | 1 | 5 |
| | | 4 | 386 | 6 | 2 | 3 |

To standardize for the heterogeneity within and between tumor samples with regard to cellularity, DNA was extracted from the pellets which contain nuclei and other cellular debris of the homogenized tumor specimens. Expression of the total amount of GTP bound to Ras per μg of extracted DNA more accurately reflects the amount of activated Ras in tumor cells. In sarcoma tissue, the amount of GTP bound to Ras ranged between 33–61 fmol/μg DNA (Table II, FIG. 3) with an average value of 46.0±7.0 fmol/μg DNA. The four NF1 benign neurofibroma specimens had between 1–12% or an average of 6.0±2.5% Ras in the GTP bound state (Table II, FIG. 3). This represented 8–20 fmol GTP/μg DNA or an average 13.3±2.6 fmol GTP/μg DNA (Table II, FIG. 3). Levels of activated Ras-bound GTP in the benign neurofibromas, expressed either as a percentage of total Ras or in total amounts per μg DNA, were approximately one-third the levels detected in the neurogenic sarcomas. In the four non-NF1 benign schwannomas, the percent of activated Ras-bound GTP ranged between 1–2% with an average 1.3±0.3% (Table II, FIG. 3). In standardized amounts this represented 2–5 fmol GTP/μg DNA or an average 3.5±0.6 fmol GTP/μg DNA (Table II, FIG. 3). These levels of activated Ras-bound GTP in the benign schwannomas were approximately 8% and 21% of the levels found in the NF1 neurogenic sarcomas and neurofibromas, respectively.

While analysis of positive control RT8 fibroblasts demonstrated that the method of the invention yields results for cultured cells that are comparable to the $^{32}PO_4$-incorporation Ras loading technique, the use of which is limited to cells in culture, this example demonstrates that Ras-bound guanine nucleotide levels can also be measured in tissues from a mammal, such as a human patient.

There are several advantages of the method of the invention, in addition to its use in tissues. First, the assay does not require pre-incubation in phosphate-free medium, which decreases intracellular levels of phosphorylated intermediates including ATP, potentially altering multiple biochemical processes (Atkinson, D. E. (1968) Biochemistry 7:4030–4034). Second, the method provides for the determination of G protein-bound GTP or G protein-bound GDP standardized to cellular protein or cellular DNA content for more accurate comparison between samples and tissue types. The method also avoids the use of large amounts of radiolabelled phosphate required for the $^{32}PO_4$-incorporation Ras loading technique (Satoh, T., et al. (1990) PNAS 87:5993 supra; Satoh, T. et al. (1990) PNAS 87: 7926 supra; DeClue, J. et al. (1992) Cell 69:265–273; Basu. T. et al. (1992) Nature 356:713–715).

The method of the invention, preferably the enzymatic technique of the method, is applicable to the study of pathological systems where Ras-mediated or other G protein-mediated signaling is implicated. Preferably, at least approximately 5–10 million cells from cell culture or tumor tissue are utilized. Studies may require more tissue if a tumor is small or diffuse within a nontumor cellular matrix. The amount of tissue required will depend on the cellular density of the tissue. Thus, tumors with a large amount of non-cellular necrotic material will require relatively more tissue than tumors with densely packed cells, and in some of the examples described herein, 2 cm$^3$ of tissue were assayed. It is also preferred that specimens be flash frozen (for example, within 30 sec. of removal from the patient, as disclosed herein), although the exact time before significant phosphatase and protease activity leads to degradation of the samples is not known. The measurements described herein of Ras-bound guanine nucleotides are from the entire tumor sample, and do not specify the levels specifically found in the tumor cells only, as distinct from infiltrating and surrounding cells. Hence, both tumor and non-tumor cells (a variable and occasionally significant proportion of the cells in some tumors) within the specimens, contribute to the measured values of G protein-bound GTP and G protein-bound GDP. The sensitivity of the method of the invention has the advantage of allowing detection of elevated G protein.GTP levels in such tissue samples.

It is within the scope of the method of the invention that an antibody specific for a G protein of interest would be used to isolate the G protein of interest bound to GTP or GDP. It is also within the scope of the method of the invention that an antibody specific for the Ras.GTP activated form or the Ras.GDP form would be utilized to specifically isolate Ras.GTP or Ras.GDP, respectively, for analysis of Ras-bound guanine nucleotides in various tissues.

Expressing levels of activated Ras in the specimens as a percentage ([GTP]/[GDP+GTP]×100), or standardized amounts of Ras-bound GTP per μg DNA, minimizes a potential source of variability between tumors due to the amount of acellular areas in a tumor. The acellularity of a tissue may alter the measured levels of Ras-bound guanine nucleotides if expressed in terms of protein. The conclusions regarding the levels of activated Ras in the three tumor groups were similar using standardization factors of cellular non-nuclear protein content or cellular DNA content in these examples.

Example 4

Detection of Ras-GTP and Ras-GDP in Breast Tumor

Overexpression of the erbB-2 gene product, the HER-2/neu receptor, by as much as 30-fold occurs in up to 40% of breast cancers and appears to correlate with a more malignant phenotype (Slamon, et al., (1989), Science, 244:707–712; and Slamon, D. J., et a., (1987), Science, 235:177–182). Similarly, the erbB-1 gene product, the epidermal growth factor (EGF) receptor, is overexpressed in approximately 45% of breast cancers and appears to be an adverse prognostic factor (Sainbury, J. R., et al., (1987), Lancet, 1398–1402). The erbB-2 receptor and the EGF receptor are tyrosine kinases that signal through the Ras/mitogen-activated protein (MAP) kinase pathway, implicating Ras activation in breast cancer (Slamon, D. G., et al., (1987), Science, 235:177–182). In erbB-2 and erbB-1 overexpressing breast tumors, and potentially in other breast cancers, there may be a high percentage of Ras molecules in the active GTP-bound state. Proc. Natl. Acad. Sci. USA, 84,7159–7163; and DiFiore, P. O., et al., (1987), Cells, 51:1063–1070). Overexpression of the EGF receptor in fibroblasts results in cellular transformation and is associated with increased activation of Ras and of the Ras/MAP kinase pathway (Satoh, T., et al., (1990), Proc. Natl. Acad. Sci. USA, 87:7926–7929). Defining which breast cancers show increased Ras activation will provide determination of appropriate treatment strategy using inhibitors of Ras function and of the Ras/MAP kinase pathway. Thus, the invention is useful for determining an appropriate mechanism-based treatment strategy for breast cancer.

It is most relevant to ask in what percentage of breast cancers is Ras in a more activated state than in normal breast tissue since it is only activated Ras molecules that can interact with downstream effector molecules. Clearly the presence of more Ras molecules in a cell does not necessarily lead to more activated Ras molecules because the activation state of Ras is tightly regulated by RasGAP's and guanine nucleotide exchange factors. The most accurate way to determine whether there are an increased number of Ras molecules in the activated state in breast cancer is to directly measure Ras-bound GTP and GDP in breast tumors. Because standardized amounts of Ras.GTP and Ras.GDP are measured using the method of the invention, an accurate percentage of Ras.GTP is calculated. In addition, the sum of Ras.GTP and Ras.GDP will provide a measurement of Ras expression in breast cancer cells.

Measurement of Ras.GTP and GDP
Breast Tissue Extraction

An alternative protocol for procurement of breast cancer cells is used: immediately after resection of the breast tumor, scrapings from the tumor surface are taken and applied to a glass slide which is rapidly frozen on dry ice and stored at $-80°$ C. A typical scraping provides approximately $1\times10^6$ cells per slide. The cells are extracted at a convenient time by lysing them directly on the slide in an ice-cold Hepes-based buffer system containing protease inhibitors and 1% Nonidet P-40. A major advantage of the scraping procedure is that it provides predominantly tumor cells with very little underlying stroma and connective tissue. Thus, approximately four slides of cells are needed to measure Ras.GTP and Ras.GDP because approximately $5\times10^6$ cells are needed for the method of the invention.

It is an advantage of the invention, and understood by one of ordinary skill in the art, that once the cell lysate is prepared, determination of G protein-bound GTP and G protein-bound GDP levels is performed by the procedures described above whether the cells were grown in culture or whether the cells were excised from tumor tissue or other disease tissue.

Immunoprecipitation of Ras

An aliquot of the cell lysate is saved to measure protein and DNA content (as described below). The remainder of the lysate is centrifuged and supernatants applied to small Sephadex G25 columns to remove cytosolic GTP and GDP. Immunoprecipitation of Ras.GTP and Ras.GDP is performed as described above for analysis of tissue samples.

Measurement of GTP and GDP

The eluted GTP is converted to ATP in the presence of ADP and NDP kinase and the ATP is measured using luciferase and luciferin (Scheele, J. S., et al., (1995), Proc. Natl. Acad. Sci. USA, 92:1097–1100) as described above.

GDP is measured by conversion to $[\gamma^{-32}P]GTP$ using NDP kinase and $[\gamma^{-32}P]ATP$. The resulting radioactive GTP product is separated from ATP by TLC and is quantitated by liquid scintillation counting as described above.

Calculation of Standardized Amounts of Ras-Bound GDP and GTP

The amounts of GDP and GTP in the samples are determined from standard curves as described above. The standardized amounts are expressed as fmol of GTP or GDP per µg DNA or per milligram protein.

Measurement of Protein and DNA

Protein and DNA are measured by the Bradford method (Bradford, M. M., (1976), Anal. Biochem., 72:248–254) and by fluorescence (Brunk, C., et al., (1979), Anal. Biochem., 92:497–500), respectively. The Bradford assay is sensitive to 1 µg of protein, and using the fluorescent dye bisbenzimidazole, 10 ng of DNA can be measured.

Example 6

Screening Ras Inhibitors in Cell Lines Using the Method of the Invention

The method of the invention is useful to screen candidate compounds for an affector of G protein activation. Such affector compounds include, but are not limited to, regulators of Ras activation or of RasGAP activity. The screening method involves contacting cells with a candidate compound, followed by assaying the cells for a change in the level of G protein activation.

The cells useful in the screening method may be cultured transformed cells (such as Ras-transformed RT8 cells) or they may be tissue from an animal model (such as Ras activation-associated tumor tissue from a mouse). Concentrations of test compounds in contact with the test cells or dosages administered to a test animal are readily determined by one of ordinary skill in the art.

The effect of Ras inhibitors (or other G protein inhibitors) on the morphology of the transformed test cells or transformed tissue in an animal is correlated with the level of G protein activation. Such a correlation allows evaluation of candidate inhibitors for usefulness in the treatment of Ras activation-associated diseases.

For in vitro screening, cultured G protein transformed cells are contacted with the candidate compound at a concentration and for a time sufficient to affect activation of the G protein of interest, such as Ras. Cells are harvested rapidly by washing once in ice cold phosphate-buffered saline and extracted in situ in a detergent-based lysis buffer. Ras is immunoprecipitated from cell lysates and Ras.GTP and Ras.GDP are measured as described above.

For in vivo screening, a candidate G protein activation inhibitor is administered to a mammal having tissue transformed by G protein activation. Preferably, the candidate compound is administered in a pharmaceutically acceptable carrier. The transformed tissue of the animal is sampled and the amount of GTP and GDP bound to Ras or other G protein is determined by the method of the invention as described above for assay of tissue samples. An alteration in the amount of Ras activation, measured as the standardized amount of Ras in the activated Ras.GTP state, is monitored relative to G protein-transformed tissue from an untreated mammal for each candidate compound. Candidate inhibitors which reduce the level of G protein activation are selected for further study.

USE

Methods are disclosed herein to measure standardized amounts of Ras-bound GDP and GTP in cultured cells and tissue expressing Ras. The GDP measurement relies on the extremely high specific activity of commercially available [$\gamma$-$^{32}$P]ATP. The GTP measurement relies on the exquisite sensitivity of luciferase for measuring ATP (Lemasters, J. J. and Hackenbrock, C. R. (1978) Methods Enzymol. 57:36–50). The method avoids exposing cells to phosphate-free medium which can adversely affect the accuracy of the GTP and GDP measurements. It also avoids the danger and high cost of using large amounts of radiolabelled orthophosphate to label cells in culture.

The method has the advantage of being useful for measuring G protein-bound GTP levels and G protein-bound GDP levels in tissue samples for the purpose of determining G protein activation levels in cells and tissue from a patient. The method is applicable to the measurement any G protein-bound guanine nucleotides for which a specific antibody to the G protein is obtainable. The non-limiting examples provided herein describe the method applied to the G protein, Ras, and the diagnosis of disease associated with an increase in G protein-bound GTP in tissue samples. Such a measurement is not possible by the $^{32}$PO$_4$-incorporation method since $^{32}$PO$_4$ incorporation is applicable only to cells in tissue culture.

The method of the invention is also useful in providing a screening method for candidate compounds that affect the regulation of G protein activation in cultured cells or in tissue.

The instant invention is shown and described herein in what is considered to be the most practical, and the preferred embodiments. It is recognized, however, that departures may be made therefrom which are within the scope of the invention, and that obvious modifications will occur to one skilled in the art upon reading this disclosure.

What is claimed is:

1. An assay method for determining the amount of a G protein having bound guanosine 5'-triphosphate (GTP) in a cell of a mammal, wherein the G protein is a G protein of a Ras G protein family, comprising:
    a) obtaining a sample of test cells which have not been exposed to radiolabelled orthophosphate;
    b) isolating a G protein of the Ras G protein family from a lysate of said test cells to provide a G protein sample;
    c) eluting G protein-bound GTP from said isolated Ras protein to provide eluted GTP;
    d) converting said eluted GTP to adenosine 5'-triphosphate (ATP); and
    e) determining the amount of said ATP of said G protein sample as a measure of the amount of G protein-bound GTP.

2. The assay method of claim 1, further comprising:
    selecting an internal standard from the group consisting of non-nuclear cellular protein of said test cells and cellular DNA content of said test cells;
    calculating the amount of said GTP with respect to the amount of said internal standard to provide a standardized amount of G protein-bound GTP for said test cells;
    comparing said standardized amount of G protein-bound GTP with a standardized amount of G protein-bound GTP determined for a control sample of cells.

3. The method of claim 2 further comprising:
    deducing a probability of activation of a G protein of the Ras G protein family protein based on a difference between the standardized amount of G protein-bound GTP determined for said control sample of cells and the standardized amount of G protein-bound GTP determined for said test cells.

4. The method of claim 2, wherein the standardized amount of G protein-bound GTP is at least 2-fold higher in said test cells relative to the standardized amount of G protein-bound GTP in said control sample of cells.

5. The method of claim 2, further comprising:
    eluting G protein-bound GDP from said isolated G protein to provide eluted guanosine 5'-diphosphate (GDP);
    converting said eluted GDP to detectable GTP;
    determining the amount of said detectable GTP in said G protein sample for said test cells;
    calculating the amount of said G protein-bound GDP with respect to the amount of said internal standard to provide a standardized amount of G protein-bound GDP for said test cells;
    comparing said standardized amount of detectable GTP with a standardized amount of detectable GTP determined for a control sample of cells.

6. The method of claim 5 further comprising:
    deducing a probability of activation of a G protein of a Ras G protein family based on a difference between:
    i) a ratio of standardized amount of G protein-bound GTP to the sum of the standardized amount of G protein-bound GTP and GDP, calculated for test cells; and
    ii) a ratio of standardized amount of G protein-bound GTP to the sum of the standardized amount of G protein-bound GTP and GDP, calculated for said control sample of cells.

7. The method of claim 7, wherein the ratio in step i is at least 2-fold higher than in step ii.

8. The method of claim 1, wherein said isolating is by immunoprecipitation with an antibody specific to said G protein.

9. The method of claim 7, wherein said antibody is Y13-259, American Type Culture Collection Accession No. ATCC CRL 1742.

10. The method of claim 5, wherein said converting of eluted GDP to detectable GTP is by enzymatic reaction with nucleotide diphosphate kinase (NDP) kinase in the presence of $\gamma$-$^{32}$PO$_4$.

11. The method of claim 1, wherein said converting of eluted GTP to ATP is by NDP kinase; and said determining of the amount of GTP-converted ATP in said sample is by measuring light emitted by luciferase reaction with said GTP-converted ATP.

12. A method according to claim 3 or claim 6, wherein said test cells are from a tissue extracted from said mammal.

13. The assay method of claim 1, further comprising:

(f) obtaining a sample of control cells which have not been exposed to radiolabelled orthophosphate, the control cells being derived from the same species as the test cells;

(g) isolating said G protein from a lysate of said control cells to provide a G protein sample;

(h) eluting G protein-bound GTP from said isolated G protein of step g to provided eluted GTP;

(i) converting said eluted GTP of step h to ATP;

(j) determining the amount of said ATP of said control sample as a measure of the amount of G protein bound GTP;

(k) comparing the amount determined in step I with the amount determined in step e; and (l) deducing a probability of G protein activation based on a difference between the amount determined in step i with the amount determined in step (e).

* * * * *